(12) United States Patent
Sugarbaker

(10) Patent No.: US 6,383,162 B1
(45) Date of Patent: May 7, 2002

(54) APPARATUS AND METHOD FOR ABDOMINO-PELVIC CHEMOTHERAPY PERFUSION AND LAVAGE

(76) Inventor: Paul H. Sugarbaker, 3629 Fulton St., NW., Washington, DC (US) 20007

( * ) Notice: Subject to any disclaimer, the term of this patent is extended or adjusted under 35 U.S.C. 154(b) by 0 days.

(21) Appl. No.: 09/438,479

(22) Filed: Nov. 12, 1999

(51) Int. Cl.$^7$ ................................................ A61M 1/00

(52) U.S. Cl. .............................. 604/28; 606/1; 600/201

(58) Field of Search ........................... 606/1, 130, 213; 604/26, 28; 128/849–852, 868, 870, 874, 887, 888; 600/201

(56) References Cited

U.S. PATENT DOCUMENTS

| | | | |
|---|---|---|---|
| 2,403,400 A | | 7/1946 | Reyniers ........................ 128/1 |
| 2,473,033 A | * | 6/1949 | Letac ........................... 600/21 |
| 3,850,172 A | | 11/1974 | Cazalis ........................ 128/204 |

(List continued on next page.)

FOREIGN PATENT DOCUMENTS

WO      WO 86/06272      * 11/1986 ............ A61F/13/00

OTHER PUBLICATIONS

Sugarbaker, Paul H., *Management of Peritoneal Surface Malignancy Using Intraperitoneal Chemotherapy And Cytoreductive Surgery*, Ludann Press, Nov. 1998.

Takashi Fujimura, et al., *Continuous Hyperthermic Peritoneal Perfusion for the Treatment of Peritoneal Dissemination in Gastric Cancers and Subsequent Second–Look Operation*, Cancer 65 pp. 65–71, 1990.

Motomichi Torisu et al., *New Approach to Management of Malignant Ascites with a Streeptococcal Preparation, OK–432.*, Surgery, Mar. 1983, pp. 357–364.

*Primary Examiner*—Glenn K. Dawson
*Assistant Examiner*—Jennifer Maynard
(74) *Attorney, Agent, or Firm*—Nath & Associates PLLC; Gary M. Nath; Marvin C. Berkowitz

(57) ABSTRACT

An abdomino-pelvic perfusion and lavage apparatus is disclosed to which skin surrounding an incision formed through an abdominal wall of a patient can be attached and suspended. The apparatus includes a containment vessel impermeable to water and air, having a wall having a base, wherein the wall has an upper end with a perimeter which defines an upper opening, a lower end with a perimeter which defines a base opening, a cranial end with a perimeter edge which defines an opening, and a caudal end with a perimeter edge which defines an opening. The containment vessel can be carried by a table on which a patient is positioned. Scaffolding carried by the containment vessel supports and elevates the skin surrounding the incision made through the abdominal wall of the patient and thereby forms a well above, and extending into, an abdomino-pelvic cavity. A plurality of fluid ports communicate through the wall of the containment vessel. The cranial opening and the caudal opening can be sealed around the patient's torso. A base seal can seal the base of the containment vessel to the table. Perfusion fluid can be supplied from a reservoir to one of the fluid ports communicating through the wall of the containment vessel and delivered to the well and can be withdrawn from the well and returned to the reservoir. A removable cover can be sealed over the upper opening of the containment vessel. The cover can be removed for visual inspection and manual manipulation of the lavage fluid and the patient's viscera. An air evacuation system can be connected to the fluid port and can evacuate aerosols and gasses from within the containment vessel. A heater can be used to heat the perfusion fluid when carrying out hyperthermic perfusion. The apparatus can be left in place on a patient for up to 5–10 days particularly when using cell-cycle specific chemotherapy agents which require long-term contact with tissues in order to achieve their optimal effect. Similarly, the apparatus can be used for repeated access to the abdomino-pelvic space in patients with peritonitis or pancreatitis.

45 Claims, 8 Drawing Sheets

U.S. PATENT DOCUMENTS

| | | | |
|---|---|---|---|
| 3,907,389 A | 9/1975 | Cox et al. ....................... | 312/1 |
| 4,275,719 A * | 6/1981 | Mayer ........................ | 128/132 |
| 4,550,713 A | 11/1985 | Hyman | |
| 4,844,074 A | 7/1989 | Kurucz ........................ | 128/401 |
| 4,865,049 A * | 9/1989 | Gatti ........................... | 128/849 |
| 4,872,458 A | 10/1989 | Kanehira et al. ........... | 128/401 |
| 5,003,991 A | 4/1991 | Takayama ................... | 128/784 |
| 5,178,162 A * | 1/1993 | Bose ........................... | 128/849 |
| 5,336,171 A | 8/1994 | Sugarbaker .................. | 604/24 |
| 5,437,683 A | 8/1995 | Neumann et al. ........... | 606/151 |
| 5,620,407 A * | 4/1997 | Chang ......................... | 600/21 |

\* cited by examiner

APPARATUS AND METHOD FOR ABDOMINO-PELVIC CHEMOTHERAPY PERFUSION AND LAVAGE

FIELD OF THE INVENTION

This invention relates to surgical appliances and methods, and more particularly to an improved apparatus and method for perfusion and lavage of an abdomino-pelvic area both during and after surgery; and in particular when using cell-cycle specific chemotherapy drugs which require long-term contact with tissues in order to achieve their optimal effect. By allowing prolonged and repeated access to an abdominal cavity the apparatus can assist in the management of serious intra-abdominal infections. Additionally, by permitting repeated access to the abdominal cavity, the apparatus is adapted for non-oncologic use in the treatment of intra-abdominal sepsis, peritonitis and pancreatitis.

BACKGROUND OF THE INVENTION

One of the mechanisms of the dissemination of gastrointestinal and gynecologic cancers is the intraperitoneal dissemination of the disease. Without special treatments all patients with peritoneal dissemination of cancer die; most patients die within one year. In an attempt to improve the control of intra-abdominal cancer, large doses of anti-cancer drugs can be injected directly into the peritoneal cavity. This therapy has shown beneficial effects in selected patients. Also other therapies in addition to intraperitoneal chemotherapy have been developed in an effort to better control the peritoneal dissemination of cancer.

It has been observed that hyperthermia seems to have a direct anti-cancer effect and synergy with some types of anti-cancer drugs, so that the toxicity for cancer cells is significantly increased at an elevated temperature. Examples of chemotherapy drugs which have been found effective in hyperthermic perfusion of the peritoneal cavity are cisplatin (CDDP) and mitomycin C (MMC). Accordingly, hyperthermic peritoneal lavage with a chemotherapy solution has been utilized to wash away free cancer cells in the peritoneal cavity by irrigation with a large volume of perfusate, to kill cancer cells by hyperthermia, and to kill cancer cells by the direct effects of chemotherapy. However, due to the inherent long and short term toxicity of chemotherapy solutions to operating room personnel, lavage with a chemotherapy solution can only be safely performed in a contained environment that prevents splashing, spillage and aerosol contaminants from escaping into the local atmosphere creating an environmental hazard to health care personnel.

Conventional techniques employing hyperthermic peritoneal lavage rely upon the use of a tube for infusion of heated fluid into the peritoneal cavity, and one or more drain tubes for removing the perfusate from the cavity. The lavage fluid can contain acid to lower pH, sugar to elevate glucose levels, antibiotics, chemotherapy (using single or multiple agents) and fibrinolytic agents, and can be exchanged to irrigate away cancer cells, fibrinous debris and other intra-abdominal contaminants. The tubes can be inserted through small stab incisions formed in a wall of the abdomen and guided by the surgeon into a general anatomic site in which irrigation is desired, or the surgeon can make a larger incision and visually place the tubes for appropriate irrigation of the peritoneal cavity.

Direct manipulation of the tubes and of the patient's viscera during chemotherapy perfusion of the abdomino-pelvic cavity in order to guarantee uniform distribution is impossible with the conventional stab-incision technique due to the lack of access to the patient's abdomino-pelvic cavity which is afforded to the surgeon. Although direct manipulation of the tubes and viscera may be accomplished in circumstances where large incisions are employed, the inability of these conventional open abdomen techniques to contain and prevent spillage of inherently toxic lavage fluid and its aerosols thus presents a significant risk of contamination of the surgical environment with a resultant unacceptable risk of exposure of health care personnel to toxic substances.

Heated intraperitoneal chemotherapy is used to bring as much dose intensity to the affected abdominal and pelvic surfaces as is possible. Heat by itself has been shown to have a greater toxicity for cancerous cells than for normal tissues. Heat also increases the penetration of chemotherapy into tissues. As the tissues soften in response to the heat the elevated interstitial pressure of a tumor mass may decrease thereby allowing improved drug penetration. Furthermore, heat increases the cytotoxicity of selected chemotherapy agents. This synergism occurs only at the interface of heat and body tissue, at the peritoneal surface. However, in conventional techniques the temperature of the lavage fluid is typically monitored on the inflow and outflow tubes but not throughout the peritoneal cavity, thereby reducing the accuracy of control over temperature and thus possibly increasing the danger of heat injury and reducing the effectiveness of the hyperthermic treatment.

The effectiveness of hyperthermic abdomino-pelvic perfusion using conventional techniques is further reduced because the heated chemotherapy solutions may not reach cancer cells between adherent surfaces in the deep areas of the peritoneum or mesenterium, and thus the perfusate incompletely eradicates cancer cells within the peritoneal cavity.

Moreover, assessment of the efficacy of treatments for peritoneal surface cancer by measuring the ascites volume or imaging a layer of cancer by computer tomography or ultra-sonography or the cytologic examination of ascites is remarkably ineffective in revealing residual or recurrent cancer in the peritoneal cavity.

Additionally, the inability to contain the environment within which conventional abdomino-pelvic perfusion is performed for an extended period of time further reduces its effectiveness because it limits or precludes the ability to use cell-cycle specific drugs such as 5-fluorouracil, which achieve their optimal effect through continuous long-term exposure of 5–10 days.

There are limited diagnostic methods available to establish the occurrence of peritoneal dissemination of cancer. In most patients, this pattern of dissemination is seen at the time of surgical removal of the primary gastrointestinal or ovarian cancer. In a small proportion of patients, the peritoneal recurrence of cancer can be imaged by abdominal computerized tomography. In other patients, the rise in a tumor marker can lead to the diagnosis of peritoneal dissemination. In some situations, a second look operation (SLO) is the only reliable procedure to assess the disease state of the cancer patient.

The SLO was introduced into gastrointestinal and gynecologic surgery to provide an oncologist with a means for assessing the status of the disease approximately one year after the initial operation, before advanced disease has occurred and before the reactivation of symptoms. In gynecology, especially, SLO has been gradually approved as a useful means for assessing tumor response, removing recurrent cancer, and planning subsequent treatment in the follow-up of patients with ovarian cancer.

In order to overcome at least some of the shortcomings of prior techniques, while at the same time taking advantage of the beneficial effect of intraperitoneal chemotherapy and hyperthermia in cancer therapies, a method and apparatus for continuous hyperthermic peritoneal perfusion in combination with the administration of anti-cancer drugs having synergism with hyperthermia was developed, and disclosed, in Takashi Fujimura, et al., "*Continuous Hyperthermic Peritoneal Perfusion for the Treatment of Peritoneal Dissemination in Gastric Cancers and Subsequent Second-Look Operation*", Cancer 65:65–71, 1990. Other similar methods and apparatuses are disclosed in Sugarbaker, U. S. Pat. No. 5,336,171, the contents of which is specifically incorporated herein in its entirety by reference, and Sugarbaker, "*Management of Peritoneal Surface Malignancy using Intraperitoneal Chemotherapy and Cytoreductive Surgery*", The Ludann Company, November 1998, the entire contents of which is also incorporated herein by reference. Neuman, et al., U.S. Pat. No. 5,437,683, also discloses an apparatus for repeatedly opening and closing an abdominal incision for repeated lavage of the intra-abdominal cavity.

The apparatus developed by Fujimura, et al., comprises an acrylic cylinder with a flange at each end. One of the flanges is positioned inside the abdominal wall and the other is suspended from two right-angled bars fixed to an operating table. The cylinder is open-ended and is fixed in the surgical wound made by the surgeon. It is large enough to permit the small intestine to float in the perfusate which is a heated chemotherapy solution infused into the peritoneal cavity. Tubes extend into the peritoneal cavity through the cylinder are used to introduce and remove perfusion fluid from the cavity.

Although the Fujimura, et al. apparatus solved some of the problems of prior art systems and techniques, it is intended for use only in an operating room environment while the perfusion procedure is being performed and consequently precludes use of chemotherapy agents which achieve their optimal effect through long-term contact with the tissues. It does not protect against seepage of chemotherapy solution between the acrylic cylinder and the skin. Additionally, no protection of operating room personnel from splashing, spillage or aerosols is provided.

The Sugarbaker apparatus disclosed in U.S. Pat. No. 5,336,171 is adapted to be secured in a midline abdominal incision, and comprises an open-ended cylindrical wall having an upper end projecting above the abdominal wall and a base end with means for securing and sealing the apparatus to the skin surrounding the abdominal incision, in a water-tight manner, to form a well for containing the lavage fluid used to treat the surfaces of the abdomen and pelvis. Heated lavage fluid under pressure with anti-cancer drugs are added until the abdominal and pelvic cavities are completely filled with the fluid. Although this apparatus solved some of the additional problems of prior art systems and techniques, the seals joining the apparatus to the skin surrounding the surgical incision failed to safely secure the apparatus in place and thus presented a risk of spilling the lavage fluid with consequent exposure of personnel to the chemotherapy fluids and aerosols.

The Neumann apparatus disclosed in U.S. Pat. No. 5,437, 683 is likewise adapted to be secured in an abdominal incision and comprises a fabric of plate-like securing elements that can be detachably connected to the body tissue and has a closure that can be repeatedly opened and closed. This apparatus is an adaptation of a zipper technique which seeks to provide a convenient means for the repeated opening and closing of the surgical site. This apparatus, however, is not adapted to accommodate chemotherapy lavage and thus is inapplicable for continuous hyperthermic peritoneal perfusion in combination with the administration of anti-cancer drugs having synergism with hyperthermia.

The Sugarbaker method and apparatus disclosed in "*Management of Peritoneal Surface Malignancy using Intraperitoneal Chemotherapy and Cytoreductive Surgery*", involves heated intraoperative intraperitoneal chemotherapy by an open technique characteristic in that a running monofilament suture is used to secure the skin edges surrounding an abdominal incision to a self-retaining retractor. A tent-like plastic sheet is incorporated into the sutures to create an open space beneath. A slit is made in the plastic cover to afford the surgeon's hands access to the abdomen and pelvis whereby the surgeon can manipulate the viscera during the perfusion with the result that all of the anatomic structures within the peritoneal cavity are exposed to heat and to chemotherapy. Although this latter method and apparatus further solved some of the problems of prior art systems and techniques, the self-retaining retractor and tent-like plastic sheet preclude the ability to selectively and repeatedly open and close access to the abdomino-pelvic cavity, and to reliably prevent spillage of perfusion fluid or infiltration of the fluid's aerosols into the surrounding operating room environment, and thereby also limit its safe use. Thus, it too precludes post-operative lavage coupled with the administration of intraperitoneal chemotherapy agents which achieve their optimal effect through long-term contact with the tissues.

Accordingly, there is a need for an abdomino-pelvic perfusion and lavage apparatus which is supported by an operating room table or bed upon which a patient is lying and which is sealed to the patient's anterior skin surface. It must allow for simple and secure suspension of the skin surrounding an incisional wound made through the abdominal wall. It must supply couplings for quick and easy connection of inflow and outflow tubes and temperature monitors through the wall of the apparatus. There is also a need that such an apparatus be capable of being left in place after the patient leaves the operating room so that continuous perfusion or repeated lavaging can be performed in an aseptic condition using cell-cycle specific chemotherapy agents which require long-term contact with the target tissues. Similarly, it is desirable that such an apparatus facilitate periodic manipulation of abdominal and pelvic contents and treatment in a surgical intensive care unit (SICU) without necessitating a further operation or even requiring further use of the operating room except to suture the abdomen closed. It is also desirable that the apparatus be sealable so that chemotherapy can be performed without danger of exposure of operating room and SICU personnel to chemotherapy aerosols. Moreover, a further desired feature would include openings for free access to the peritoneal cavity for both visual inspection and for the introduction of a surgeon's hands for manipulation of the viscera. It is also desirable that there be couplings for quick and easy mounting of an air evacuation system which can evacuate the chemotherapy aerosols when the appliance is opened.

Furthermore, since chemotherapy not only directly destroys tumor cells but also eliminates viable platelets, neutrophils and monocytes from the peritoneal cavity; the ability of the abdomen to resist infection is reduced. Thus, it is imperative that the apparatus be adapted to maintain a strict aseptic environment when administering chemotherapy, handling abdominal tubes and drains, and during manipulation of the viscera.

SUMMARY OF THE INVENTION

The present invention is directed to an improved abdomino-pelvic perfusion and lavage apparatus adapted for use both during and after surgery and to which skin surrounding an incision formed through an abdominal wall of a patient can be attached and suspended. More particularly, the invention relates to an abdomino-pelvic perfusion and lavage apparatus for intraperitoneal treatment of diseases disseminated through the peritoneal cavity, and especially in the hyperthermic treatment of the peritoneal dissemination of gastrointestinal, ovarian and other intra-abdominal cancers. The invention especially allows the use of heat, coupled with manipulation of the organs, in peritoneal perfusion procedures and more particularly is adapted to be left in place after the patient leaves the operating room so that repeated lavaging can be performed using cell-cycle specific chemotherapy agents which require long-term contact with the target tissues. Additionally, by permitting repeated access to the abdominal cavity, the apparatus is adapted for nononcologic use in the treatment of intra-abdominal sepsis, peritonitis and pancreatitis.

In one preferred embodiment the invention comprises a containment vessel impermeable to water and air, having a wall having a base, wherein the wall has an upper end with a perimeter edge which defines an upper opening, a lower end with a perimeter edge which defines a base opening, a cranial end with a perimeter edge which defines an opening, and a caudal end with a perimeter edge which defines an opening. A plurality of fluid ports which are capable of providing hydraulic and pneumatic communication through the wall of the containment vessel are also provided. The containment vessel is adapted to be carried by a table on which the patient is positioned.

A further aspect of the invention comprises a scaffolding that is carried by the containment vessel for supporting and elevating the skin surrounding the incision made through the abdominal wall of the patient whereby said elevated skin forms a well above, and extending into, an abdomino-pelvic cavity.

A further aspect of the invention comprises a fluid supply reservoir which serves as a source for the perfusion fluid; a first pump in hydraulic communication with the fluid supply reservoir and at least one fluid port for providing the perfusion fluid from the source to the containment vessel; a second pump in hydraulic communication with the fluid supply reservoir and at least one fluid port for returning the perfusion fluid from the containment vessel back to the source; a heater in thermal communication with a fluid containing means to heat the perfusion fluid to a temperature of about 30° C. to about 50° C. during use of the containment vessel in hyperthermic peritoneal perfusion; at least one inflow tube in hydraulic communication with the fluid port receiving the perfusion fluid from the source for providing the perfusion fluid to the well formed in the patient's abdomino-pelvic cavity; at least one drain tube in hydraulic communication with the fluid port returning the perfusion fluid to the source and having a distal intake end extended into the well in the patient's abdomino-pelvic cavity for providing the perfusion fluid from the well; at least one temperature sensor positioned in proximity with the distal intake end of the drain tube and in communication with a thermostatic control in communication with the heater.

A further aspect of the invention comprises at least one removable cover capable of being secured and sealed over the upper opening of the containment vessel to enclose the well formed therein, thereby forming a barrier to aerosols so that chemotherapy agents can be used without exposing personnel to chemotherapy aerosols, and whereby the containment vessel may be left in place on a patient who may then be returned to an intensive care unit for follow-up examinations, continuous perfusion and repeated lavaging without introducing bacterial pathogens and without necessitating use of the operating room.

A further aspect of the invention comprises an air evacuator connected in pneumatic communication with one or more fluid ports to form a low air pressure gradient across the upper opening and thereby evacuate aerosols and gases from within the interior space whenever one or more of the sealable covers is open and thereby minimizing the risk of exposure of surgical and SICU personnel to the chemotherapy aerosols and gases.

A further aspect of the invention comprises a plurality of port-seals for sealing hydraulic and pneumatic communication through any unused fluid ports. A cranial opening seal is also provided to seal hydraulic and pneumatic communication through the cranial opening between the containment vessel and a torso of the patient and a caudal opening seal is likewise provided to seal hydraulic and pneumatic communication through the caudal opening between the containment vessel and a torso of the patient. A base seal is provided to seal hydraulic and pneumatic communication between the containment vessel and the table.

DETAILED DESCRIPTION OF THE PREFERRED EMBODIMENT

Figure 1:
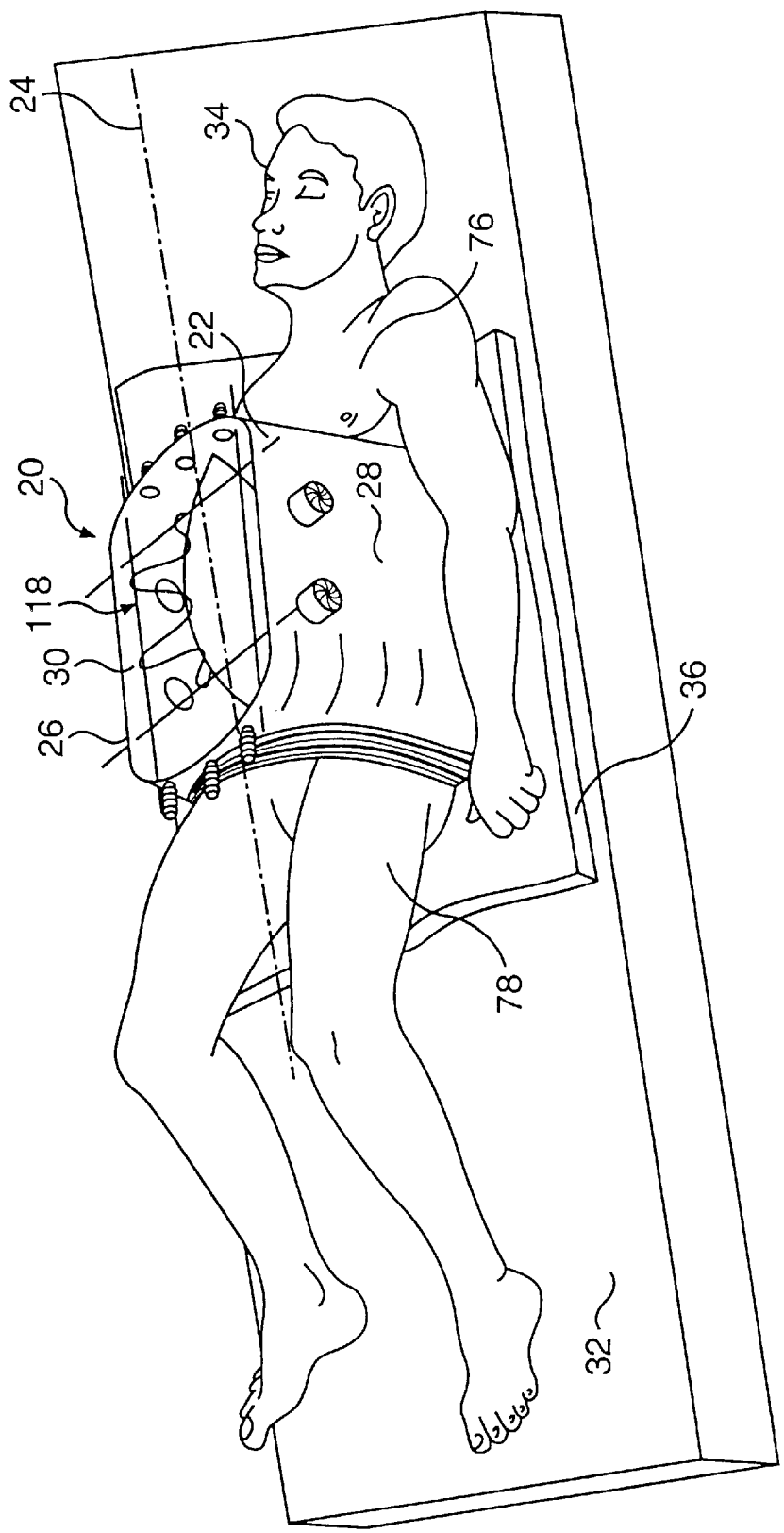
FIG. 1 is a top perspective view showing a containment vessel according to the present invention, in position over a patient on an operating table, with a cover removed to reveal an upper opening through which a scaffolding is visible and to which a skin edge surrounding an abdominal incision has been elevated and sutured.

The present invention comprises an apparatus for perfusing or lavaging the abdomino-pelvic cavity during or after surgery. More particularly, the invention is directed to an abdomino-pelvic perfusion/lavage apparatus for treatment of diseases disseminated through the peritoneal cavity, and especially in the hyperthermic treatment of the peritoneal dissemination of gastrointestinal, ovarian and other intra-abdominal cancers. The invention especially allows the use of heat, coupled with manipulation of the organs, in peritoneal perfusion procedures. Additionally, the apparatus and method of the present invention can be used in conjunction with cell-cycle specific drugs so that a lavage fluid can be maintained in the abdomino-pelvic cavity for up to 5–10 days postoperatively for long-term exposure so that the chemotherapy agents achieve their optimal effect.

Any lavage fluid employed in the prior art can be used with the apparatus and method of the present invention.

Additionally, in patients with disease states like peritonitis and pancreatitis, it can be expected that the patient need not return to the operating room on numerous occasions in order to ensure that no sepsis remained, as is utilized in the "zipper" technique or in a gauze packing technique. The patient can merely be transferred to an SICU setting with the apparatus in place where continuous perfusion, repeated gauze packing, repeated inspection or repeated lavage of the abdominal cavity can be performed. Only when the abdominal or pelvic sepsis has resolved is surgical repair of the abdominal incision in the operating room required. Multiple return visits to the operating room are to be avoided in this new approach.

The apparatus of the present invention is adapted to be supported by an operating table or other generally planar surface which also supports a patient and to elevate and secure skin around a midline abdominal incision. The apparatus comprises an open-ended containment vessel with means for supporting the skin edges surrounding the incision thereby forming a well for containing a perfusion/lavage fluid used to treat the surfaces of the patient's abdomen and pelvis. For gastrointestinal and gynecologic cancer patients, this includes a majority of sites at risk for local recurrence and peritoneal seeding. Heated perfusion fluid with anti-cancer drugs can be added until the well formed in the abdominal and pelvic cavities is completely filled with the chemotherapy solution.

In the preferred embodiment of the present invention the apparatus is adapted to be used with a cover securable over the upper end of the containment vessel to thereby confine chemotherapy aerosols and thereby maintain the operating room and postanesthesia care unit environments safe for personnel during the administration of chemotherapy. Additionally, the apparatus is also adapted to be used with its upper end open. The cover, when used, can include one or more additional smaller openings which permit the surgeon to have access to the abdominal cavity for additional functions such as: visual inspections, making incisions, further cytoreduction, excising structures, suturing, selective positioning of the inflow and outflow tubes and temperature sensing devices, and for manual manipulation of the intra-abdominal organs so that all fibrinous accumulations that can harbor cancer cells are disbursed. In cancer patients this also allows manual debridement of the narrow margins of the excision, manipulation of all peritoneal crevices, and visual inspection of all bowel surfaces. Since chemotherapy not only directly destroys tumor cells but also eliminates viable platelets, neutrophils and monocytes from the peritoneal cavity the ability of the abdomen to resist infection is reduced. Accordingly, the apparatus of the present invention is also adapted to maintain a strict aseptic environment.

Sealable ports along the wall of the containment vessel provide selective connection of inflow and outflow tubes for passage of the lavage fluid, and for temperature sensing devices extended into the abdominal cavity.

Further sealable ports along the wall of the containment vessel also provide for the selective connection of an air evacuation device and thus permit the evacuation of chemotherapy aerosols, from the interior space within the containment vessel, through the wall of the containment vessel whenever one of the access openings is open without imposing physical interference to the surgeon's access.

In a preferred embodiment the perfusion fluid is heated by use of a heater and circulated by a pair of peristaltic pumps such as found in a conventional heart-lung machine. A single inflow tube is used for supplying the perfusion fluid to the well in the abdominal cavity; and one, two, three or more drain tubes are used for draining the perfusion fluid from the abdominal cavity's well.

In one preferred embodiment one drain tube is placed beneath the patient's right hemidiaphragm, one beneath the left hemidiaphragm and the other in the pelvic cavity. If the chest cavity is entered through an incision in the diaphragm, a fourth drain tube, a chest tube, can also be used. The drain tubes should be moderately stiff, with multiple side openings, and a heat sensor should be associated with the distal end of each for monitoring the temperature of the perfusion fluid, in situ, throughout the procedure.

Sampling of the perfusion fluid drained from the abdominal cavity can be performed throughout the procedure so that the absorption of chemotherapy can be ascertained, and a geiger counter can be located over the abdomen so that any absorption from the abdomen into the systemic circulation can be estimated. This is accomplished with the use of radioactive technetium, which may or may not be attached to various molecules such as albumin. A counter over the heart can also be used to enable the amount of absorption from the abdomino-pelvic cavity to be documented in an on-line manner. Simultaneous readings in the abdominal cavity and over the heart thus enable the absorption of chemotherapy to be estimated and a maximum systemic dosage of drug delivered with the surgical or post-operative event.

The containment vessel is preferably made of a lightweight, but strong, plastic material which is impervious to water and air, such as Ultem™ made by General Electric Company, with an elliptical shape in transverse cross-section. It and other components of the apparatus can be made disposable if desired. To facilitate disposal of the used containment vessel, it can be scored at intervals to define fracture lines. The containment vessel can be made in several different sizes to accommodate different size patients and different size abdominal incisions.

In the preferred embodiments of the present invention a scaffolding can be affixed to the containment vessel for supporting and elevating the skin edges surrounding an incision made through the abdominal wall of the patient whereby the elevated skin forms a well above, and extending into, an abdomino-pelvic cavity. The skin edges surrounding the incision are elevated and connected to the scaffolding by sutures or other connecting means.

In a first alternative embodiment a series of rods are placed through sealable openings near the upper end of the containment vessel. A second embodiment uses a series of rods carried by the inner surface of the wall of the containment vessel. A third embodiment uses a scaffolding formed integrally with the inner surface of the wall of the containment vessel.

A fourth embodiment utilizes a support ring which can be elevated and hung from a suspension carried by the inner surface or the upper edge of the wall of the containment vessel. The support ring can be in the form of either an open loop or a closed loop. It can be connected to the skin edges surrounding the incision either wholly before being suspended from the suspension, wholly after being suspended from the suspension or partially before and partially after being suspended from the suspension.

The present invention has particular application where use of cell-cycle specific chemotherapy agents is desirable. An initial irrigation with a fibrinolytic agent can be first performed with the cover removed and the abdominal well open to the atmosphere. During this initial procedure all debris, cancer cells and fibrinous material can be flushed from the peritoneal cavity. Following the initial irrigation, the cover can be placed on top of the containment vessel and all fibrinolytic phase fluid can be removed from the abdomino-pelvic cavity. An irrigation with a heated chemotherapy solution can then be conducted. In the preferred embodiment of the present invention if the chemotherapy agent includes a cell-cycle specific drug, the patient, with the apparatus of the present invention remaining in place, can be transferred to a SICU where a lavage procedure can be maintained for up to 5–10 days without the need to return to the operating room except to close the abdomen at the end of the chemotherapy treatment. By using the apparatus of the present invention, the surgeon is able to re-enter the abdominal cavity with a greatly reduced risk of exposure of operating room personnel to chemotherapy aerosols. During this time, the surgeon can also manually debride the narrow margins of the excision, manipulate the peritoneal crevices, and visually inspect all bowel surfaces. After the lavage procedure is finally completed the surgeon is then able to perform all reconstructive procedures, such as bowel anastomoses and closure of the surgical incision.

The abdomino-pelvic lavage apparatus of the present invention can have uses other than in oncology. For instance, it can be used for treatment of patients with intra-abdominal sepsis by irrigating the abdominal cavity with antibiotic and fibrinolytic agents. In this way, all of the infected fibrin can be removed from the abdominal cavity. By the repeated manipulation of the abdominal contents and repeated irrigation of the abdominal cavity, pathogens will be dislodged whereby bacterial counts can be brought down to an extremely low level. The additional time that the lavage fluid is permitted to be present in the abdominal cavity by use of the invention can be of great value in eliminating sources of bacterial or fungus infection. With the removal of all contaminated fibrinous material, the patient can be expected to improve more quickly from surgery.

The foregoing aspects and many of the attendant advantages of the present invention will become more readily appreciated to those skilled in the art as the same becomes better understood by reference to the following detailed description, when taken in conjunction with the accompanying drawings, wherein like reference characters designate like parts throughout the several views.

Referring more specifically to the drawings, a first embodiment of the present invention of improved abdomino-pelvic chemotherapy perfusion and lavage apparatus 20 is indicated in FIG. 1. In this embodiment of the invention a containment vessel 22 having a generally elliptical shape in transverse cross-section with a longitudinal axis 24, is made of a material, preferably plastic, impervious to air and water. An upper perimeter edge 26 of a wall 28 defines an upper opening 30 in containment vessel 22. Containment vessel 22 is adapted to be carried by a table 32 on which a patient 34 is positioned. An absorbent-material blanket 36, which has a moisture-resistant membrane on one side, is extended laterally beyond patient 34 and is disposed between the bottom of wall 28 and table 32. As so disposed, absorbent-material blanket 36 forms an air and watertight seal between the bottom of wall 28 of containment vessel 22 and table 32.

Figure 2:
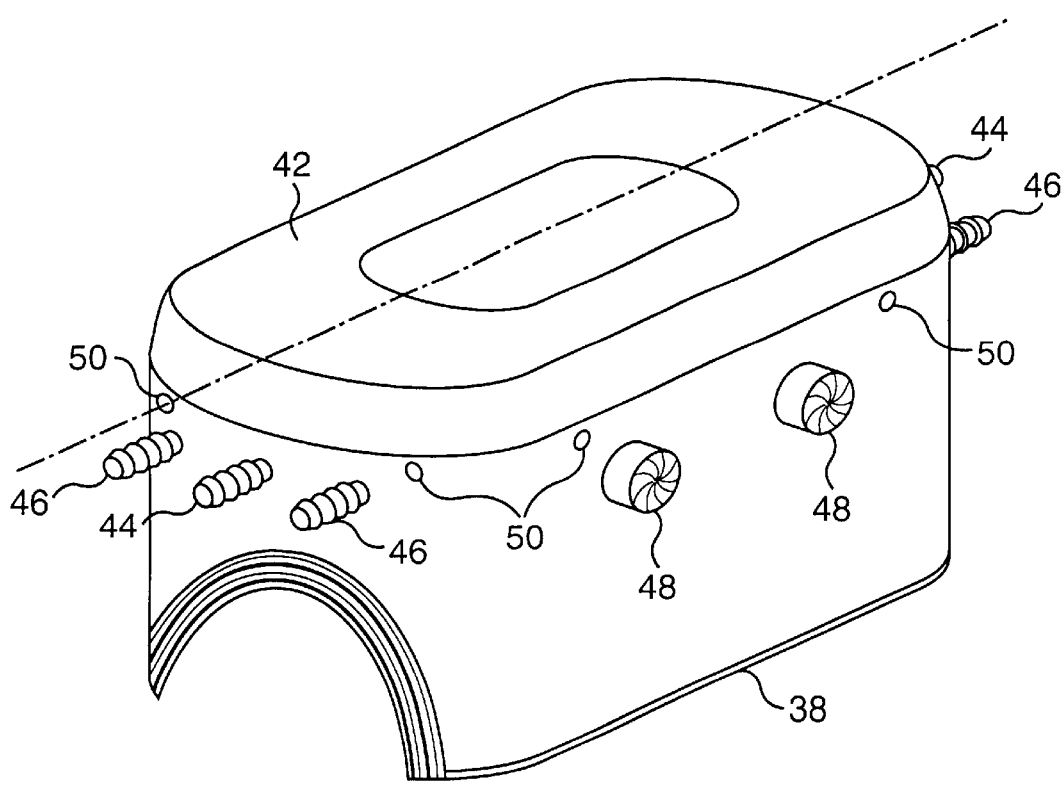
FIG. 2 is a top perspective view of the containment vessel depicted in FIG. 1, with the cover secured in place to close the upper opening, and the scaffolding in place and extending through sealable openings communicating through a wall of the containment vessel.
Figure 5:
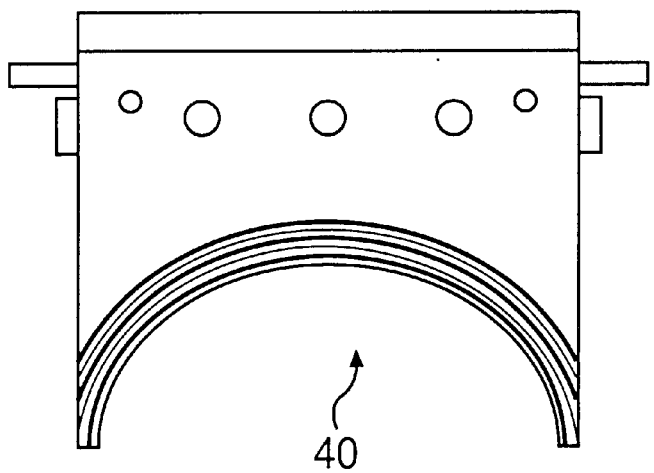
FIG. 5 is a front elevational view of the containment vessel as depicted in FIG. 2, with the cover and scaffolding in place, the rear elevational view being substantially the same.
Figure 6:
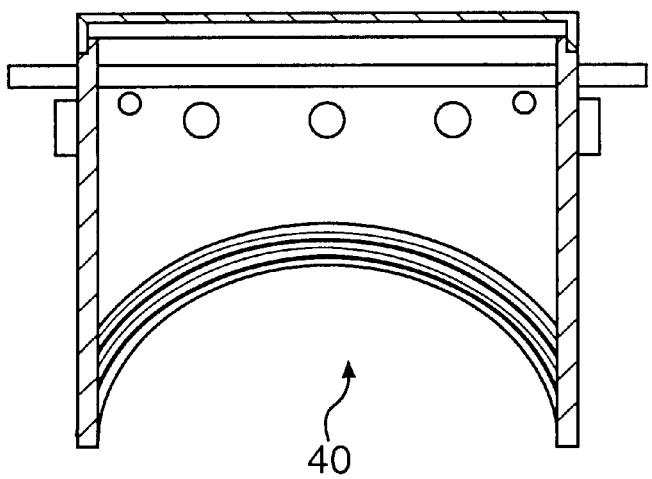
FIG. 6 is a sectional view taken through line 6—6 of FIG. 4.

Referring now to FIG. 2, a lower perimeter edge 38 of wall 28 defines a lower opening 40 (visible in FIGS. 5 and 6). One or more sealable covers 42 can be placed over upper opening 30 of containment vessel 22. A plurality of sealable inflow ports 44, a plurality of sealable outflow ports 46, and a plurality of sealable vacuum ports 48 are disposed at spaced locations around the circumference of wall 28 and communicate through wall 28. In the particular embodiment shown, a plurality of sealable openings 50 are also disposed at spaced locations along the upper portion of wall 28 and also communicate through said wall 28.

Figure 3:
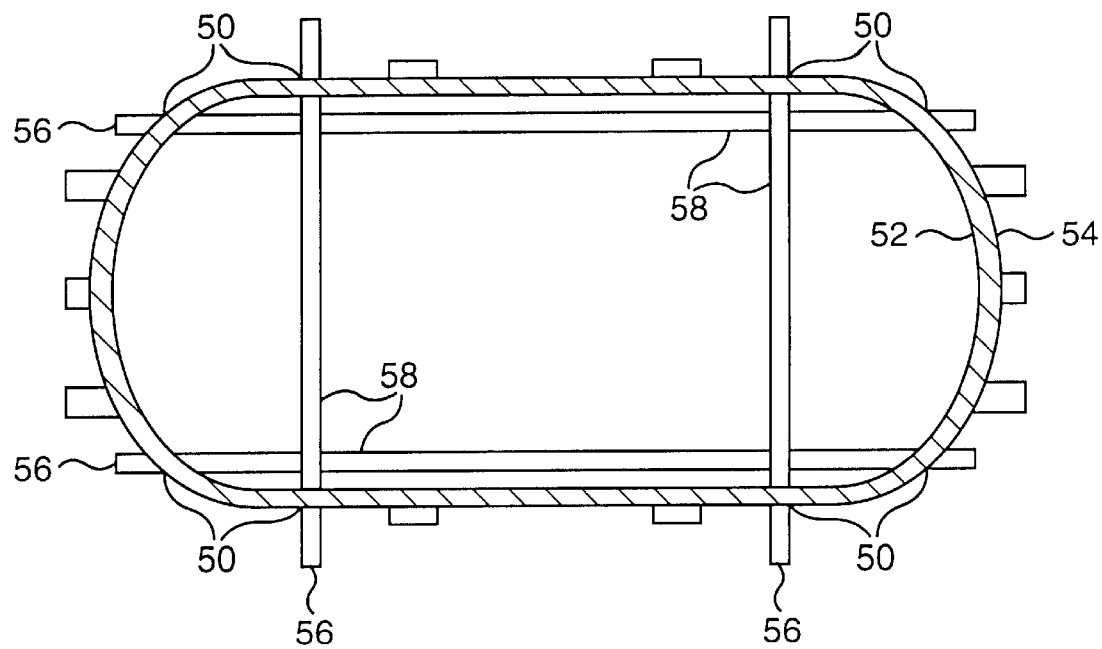
FIG. 3 is a top plan view of the containment vessel as depicted in FIG. 2, with the cover removed, and showing the scaffolding in place and extending through sealable openings communicating the wall of the containment vessel.

As is seen in FIG. 3, wall 28 has an inner surface 52 and an outer surface 54. In the embodiment shown, a plurality of rods 56 is placed through the plurality of sealable openings 50 and as thus disposed said rods 56 form a scaffolding 58 disposed between the oppositely facing surfaces of inner surface 52 of wall 28.

Figure 4:
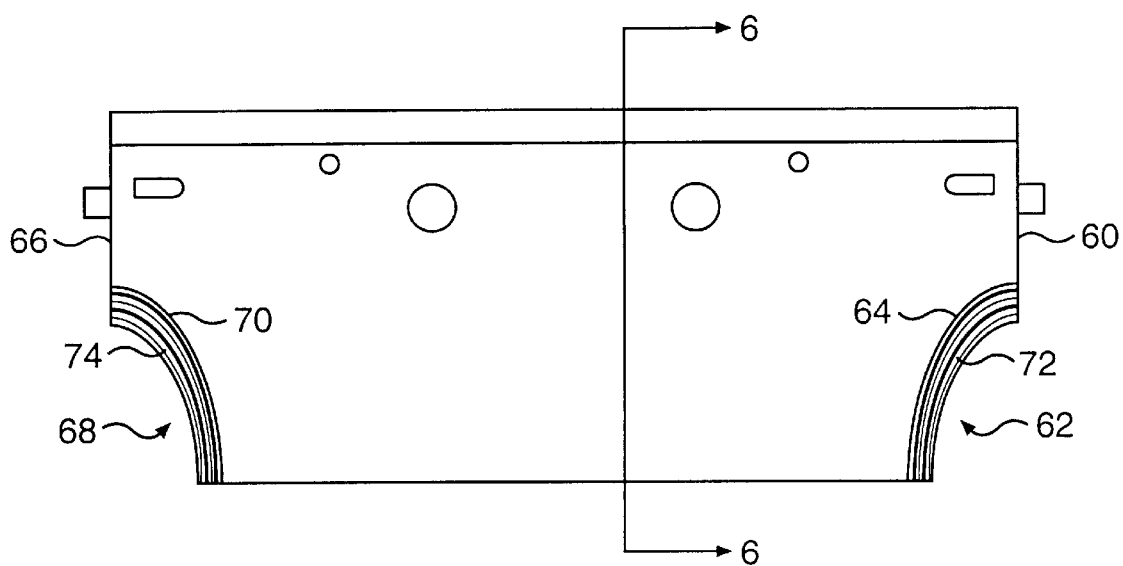
FIG. 4 is a right side elevational view of the containment vessel as depicted in FIG. 2, with the cover and scaffolding in place, the left side elevational view being substantially the same.

Referring now to FIGS. 4–6, in the preferred embodiment of the present invention containment vessel 22 has a cranial end 60 with an opening 62 defined by a generally semi-elliptical perimeter edge 64; and a caudal end 66 with an opening 68 defined by a generally semi-elliptical perimeter edge 70. A first seal 72, preferably made of a pliable membrane material which is impervious to water and air, is disposed along perimeter edge 64 of opening 62. A similar second seal 74 is disposed along perimeter edge 70 of opening 68.

Referring back to FIG. 1, cranial opening 62 and caudal opening 68 are of sufficient size such that when in use containment vessel 22 straddles patient 34 while patient 34 is disposed in lower opening 40 of containment vessel 22 and such that the bottom of wall 28 of containment vessel 22 is carried by table 32 while perimeter edge 64 and perimeter edge 70 are disposed at a proper height above and proximate to, but not in contact with, patient 34. Patient 34's upper torso 76 is disposed in cranial opening 62 and patient 34's lower torso 78 is disposed in caudal opening 68. As thus disposed, first seal 72 seals cranial opening 62 around upper torso 76 and thereby forms an air and watertight seal in cranial opening 62. Second seal 74 likewise seals caudal opening 68 around lower torso 78 and thereby an air and watertight seal in caudal opening 68.

Figure 7:
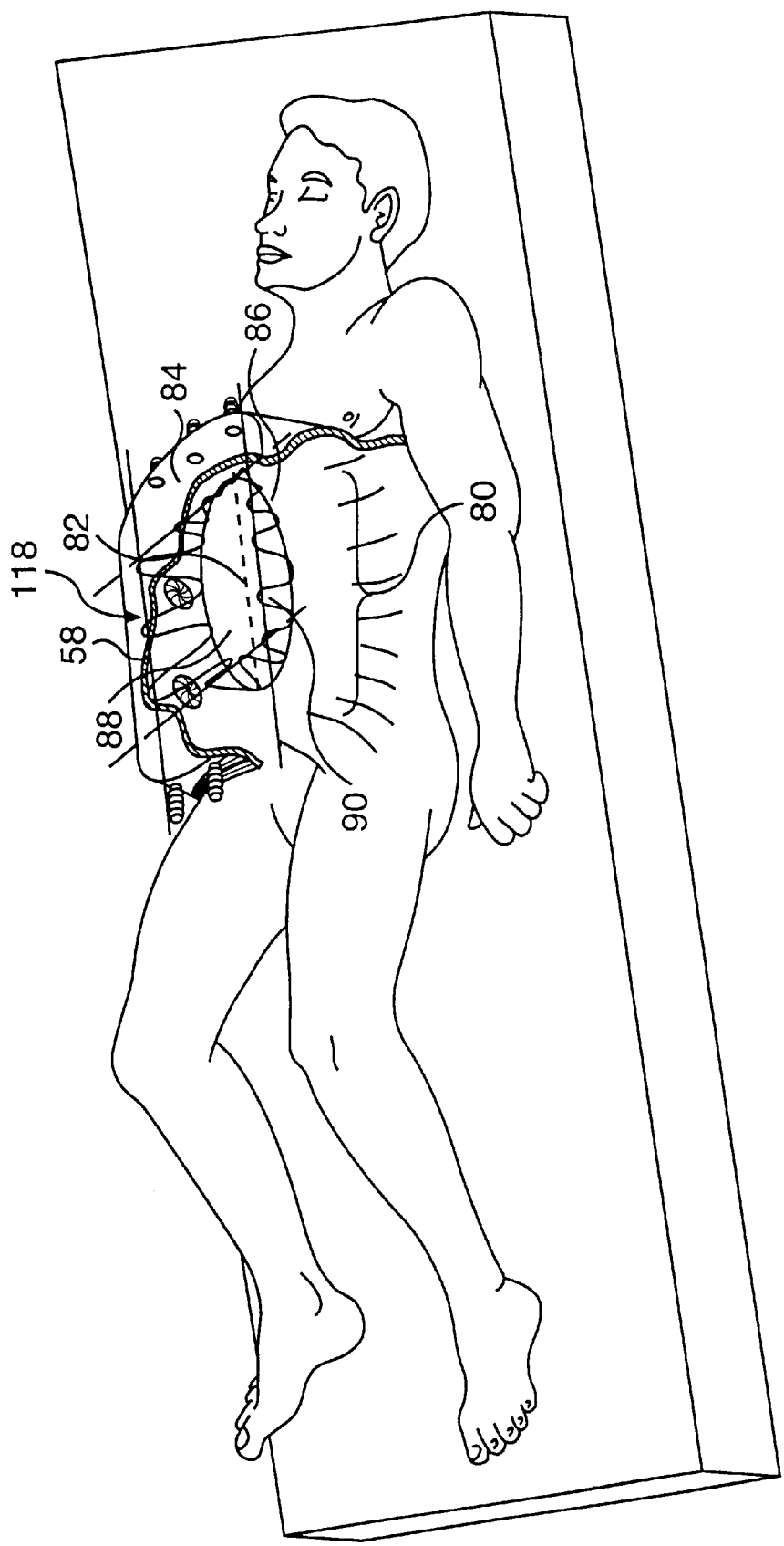
FIG. 7 is a top perspective view of the containment vessel depicted in FIG. 1 wherein a left side of the containment vessel has been cut away to better reveal the skin edges surrounding the abdominal incision which are elevated and sutured to the scaffolding thereby forming a well.

Referring now to FIG. 7, which is a cut-away view of FIG. 1 wherein a portion of wall 28 of containment vessel 22 has been cut away and removed so as to provide a view into containment vessel 22, scaffolding 58 is disposed superior to patient 34's abdominal area 80 surrounding where an incision 82 has been made or is intended to be made. After incision 82 is made in patient 34's abdominal area 80, a running suture 84 is secured through skin edge 86 surrounding incision 82. As each suture 84 is secured to skin edge 86 said suture 84 and the skin edge 86 attached thereto are vertically displaced upwardly by a surgeon (not shown) and as thus vertically displaced are disposed and secured to scaffolding 58 which then supports skin edge 86 in a vertically superior position relative to patient 34. After all sutures 84 are completed, the displacement of skin edge 86 thereby forms a well 88 above and extending into abdomino-pelvic cavity 90.

Figure 8:
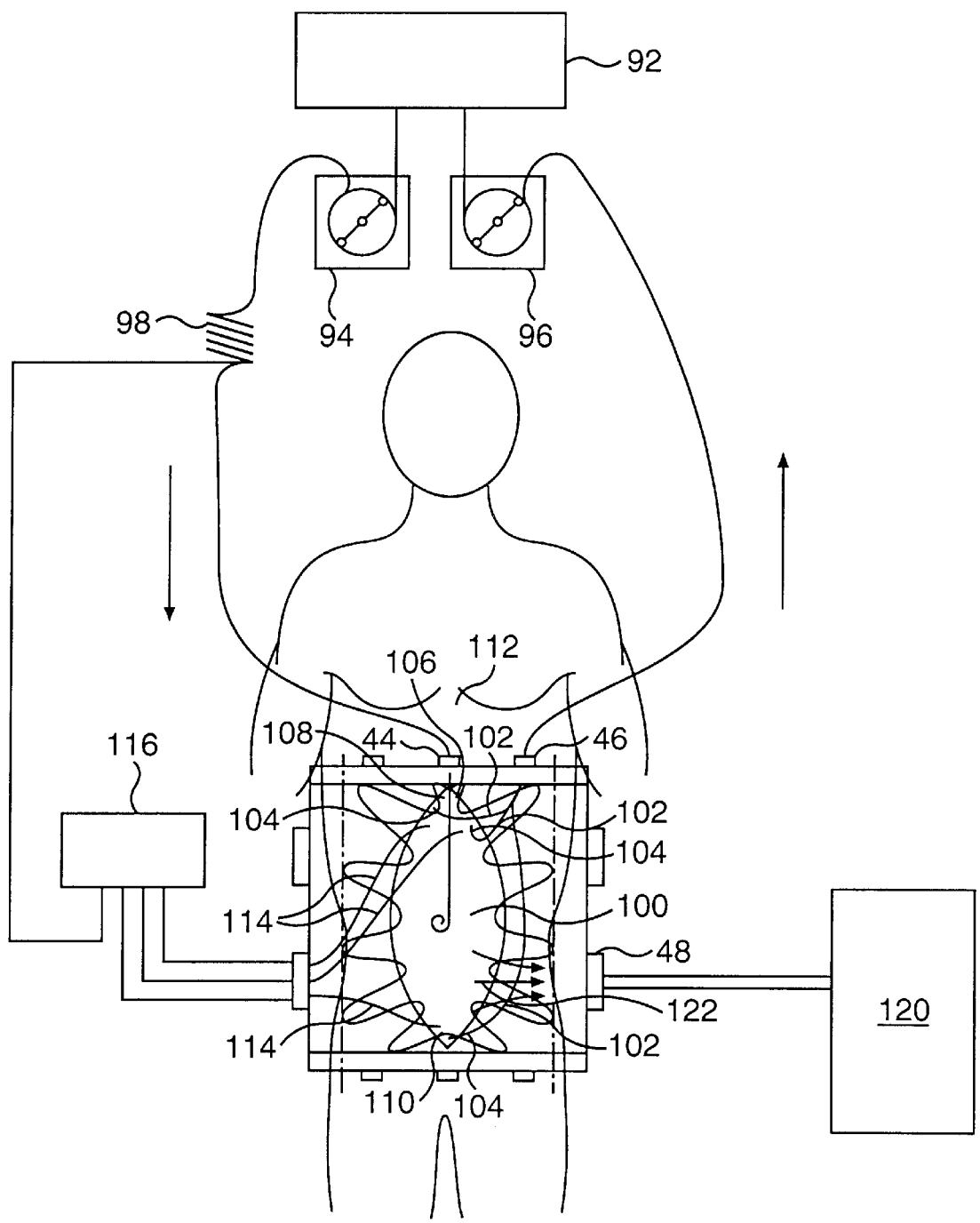
FIG. 8 is a partially schematic top plan view of the containment vessel of FIGS. 1 and 2 in use with the cover removed and the accessory devices connected in operative relationship.

Referring now to FIG. 8, perfusion fluid is provided from supply reservoir 92 through one or more of sealable inflow ports 44 communicating through wall 28 to well 88 formed in abdomino-pelvic cavity 90. Fluid is withdrawn from well 88 through one or more of sealable outflow ports 46 and returned to supply reservoir 92.

The perfusion fluid is pumped from supply reservoir 92 by first pump 94 connected in hydraulic communication with supply reservoir 92 and one or more of sealable inflow ports 44. A second pump 96 connected in hydraulic communication with one or more of sealable outflow ports 46 and supply reservoir 92 returns the fluid to supply reservoir 92. During use of apparatus 20 in hyperthermic peritoneal perfusion, a heater 98 heats the fluid to a temperature of about 30° C. to about 50° C. and preferably about 40° C. to about 50° C. and ideally about 44° C. to about 46° C. so as to maintain the temperature of the fluid in well 88 of abdomino-pelvic cavity 90 at about 42.5° C.

An inflow tube 100, which is connected in hydraulic communication with the at least one sealable inflow port 44 which is connected in hydraulic communication with supply reservoir 92 and first pump 94, delivers the fluid to well 88. At least one drain tube 102, which is connected in hydraulic communication with the at least one sealable outflow port 46 connected in hydraulic communication with supply reservoir 92 and second pump 96, withdraws the chemotherapy solution from well 88 through its distal intake end 104.

In the preferred embodiment shown in FIG. 8 there are three drain tubes 102 having distal intake ends 104 extended into well 88 and abdomino-pelvic cavity 90. Distal intake end 104 of a first drain tube 102 is disposed beneath a left hemidiaphragm 106 of patient 34, distal intake end 104 of a second drain tube 102 is disposed beneath a right hemidiaphragm 108 of patient 34, and distal intake end 104 of a third drain tube 102 is disposed in a pelvis 110 of patient 34. If the chest cavity 112 of the patient 34 is also opened, a fourth drain tube (not shown), being a chest tube, can be disposed having its distal intake end (not shown) in chest cavity 112.

One or more temperature sensors 114 are disposed in close proximity with the distal intake end 104 of each drain tube 102 to measure the temperature of the perfusion fluid within abdomino-pelvic cavity 90, said temperature sensors 114 communicating to a thermostatic control 116 connected to heater 98.

In use longitudinal axis 24 of containment vessel 22 is axially aligned with patient 34. As thus aligned, containment vessel 22 is placed over abdominal area 80 surrounding where incision 82 is to be made.

In use during chemotherapy one or more selectively removable and sealable covers 42 (as shown in FIG. 2) are disposed over upper opening 30 of containment vessel 22 thereby enclosing an interior space 118 (visible in FIGS. 1 and 7) within containment vessel 22 and thus encasing well 88. As shown in FIG. 8, air evacuator 120 is connected in pneumatic communication with one or more of sealable vacuum ports 48 to form an air pressure gradient across the upper opening 30 and when activated thereby evacuates aerosols and gases 122 from within interior space 118 whenever one or more of sealable covers 42 is open thereby minimizing the risk of exposure of surgical and SICU personnel (not shown) to the chemotherapy aerosols and gases 122.

Any unused inflow ports 44, outflow ports 46, vacuum ports 48, and openings 50 can be sealed by conventional capping or plugging means thereby forming a barrier to the chemotherapy aerosols and gases 122 so that chemotherapy agents can be used without exposing personnel to the chemotherapy aerosols and gases 122. By leaving sealable covers 42 in place and sealing unused inflow ports 44, outflow ports 46, vacuum ports 48, and openings 50, containment vessel 22 can also maintain an aseptic environment and thus be left in place on patient 34 who may then be returned to a surgical intensive care unit for follow-up examination and treatment. Maintenance of intraperitoneal lavage, repeated inspection and repeated lavage procedures can thus be accomplished without necessitating return to the operating room.

In one preferred embodiment shown in FIGS. 1–8, one sealable inflow port 44 and two sealable outflow ports 46 are disposed at cranial end 60 of containment vessel 22. Similarly, one sealable inflow port 44 and two sealable outflow ports 46 are disposed at caudal end 66 of containment vessel 22.

Figure 9:
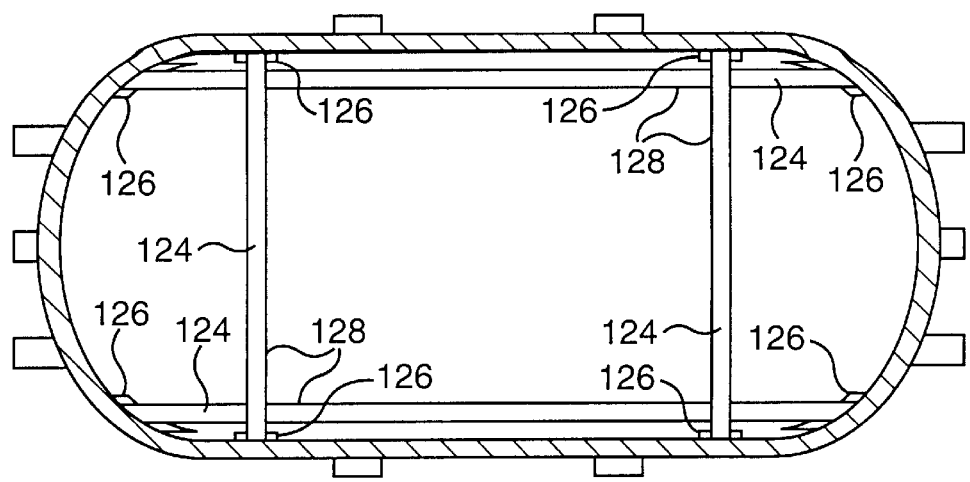
FIG. 9 is a top plan view of an alternative embodiment of the containment vessel of the present invention, with the cover removed, and wherein the scaffolding is carried by an inner surface of the wall of the containment vessel.

In an alternative embodiment shown in FIG. 9, a plurality of rods 124 are carried by supports 126 disposed on the inner surface 52 of wall 28 thereby forming an interior support scaffolding 128.

Figure 10:
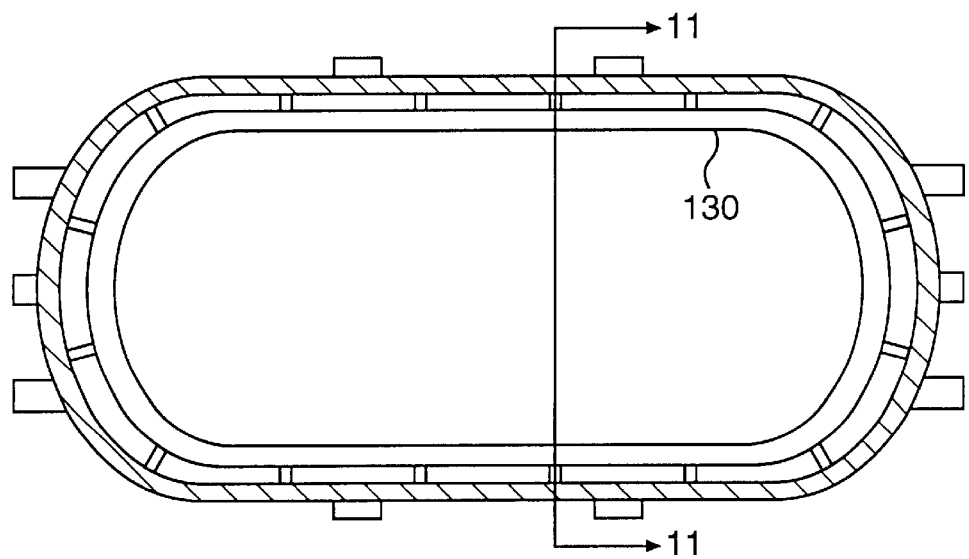
FIG. 10 is a top plan view of a further alternative embodiment of the containment vessel of the present invention, with the cover removed, and wherein the scaffolding is carried by the inner surface of the wall of the containment vessel and is integral thereto.
Figure 11:
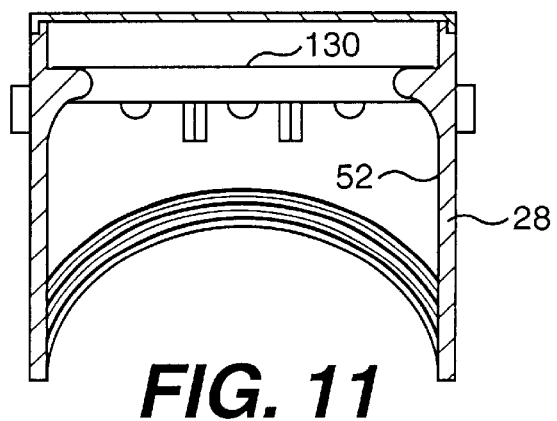
FIG. 11 is a sectional view taken through line 11—11 of FIG. 10.

In another alternative embodiment shown in FIGS. 10 and 11, an integral support scaffolding 130 is integrally formed with inner surface 52 of wall 28.

Figure 12:
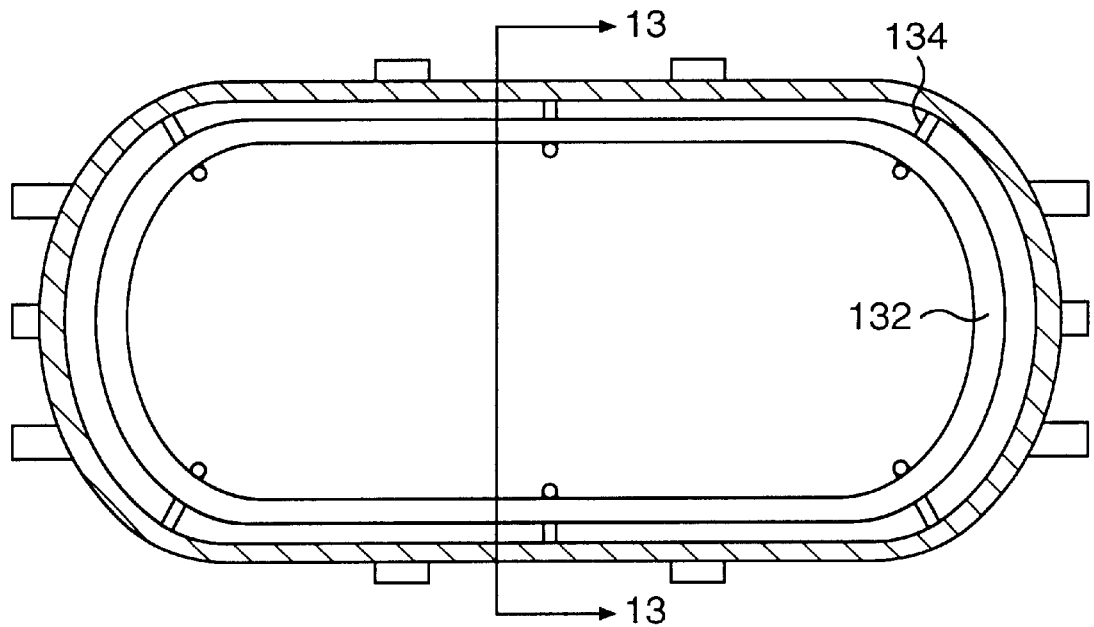
FIG. 12 is a top plan view of an alternative embodiment of the containment vessel of the present invention wherein the scaffolding is a support ring supported by a suspension carried by the inner surface of the wall of the containment vessel.
Figure 13:
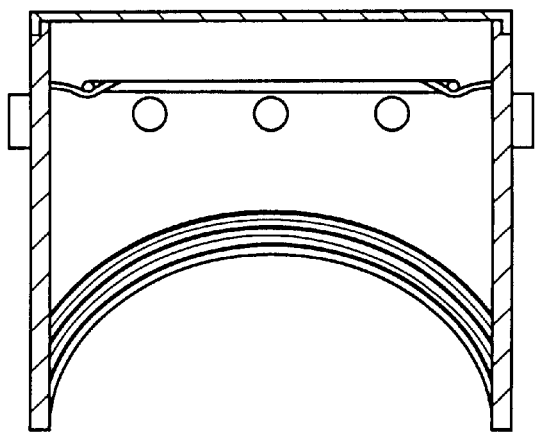
FIG. 13 is a sectional view taken through line 13—13 of FIG. 12.

In yet another alternative embodiment shown in FIGS. 12 and 13, a closed loop support ring 132, which in use defines the shape of an open end of well 88, is disposed and suspended from a suspension 134 carried by the inner surface 52 of wall 28. In a further alternative embodiment support ring 132 can be in the form of an open loop. In the embodiment shown, support ring 132 can be placed on patient 34's abdominal area 80 surrounding incision 82. Skin edge 86 surrounding incision 82 can be affixed by sutures 84 or other connecting means to support ring 132. Support ring 132, together with skin edge 86 connected thereto, can then be vertically displaced upwardly by the surgeon (not shown) to a vertically superior position and suspended from suspension 134 thereby forming well 88 above and extending into abdomino-pelvic cavity 90.

In an alternative embodiment, support ring 132 can be suspended from suspension 134 prior to being connected to skin edge 86. In yet another alternative embodiment support ring 132 can be partially connected to skin edge 86 before being suspended from suspension 134 and partially connected to skin edge 86 after being suspended from suspension 134.

In yet another embodiment, suspension 134 can be carried by upper perimeter edge 26 of a wall 28.

The invention thus provides a simple and effective apparatus for continuous perfusion and repeated lavage procedures in the abdomino-pelvic cavity, and especially an apparatus which enables the surgeon free and repeated access to the abdomino-pelvic cavity during the perfusion/lavage process and which permits accurate monitoring and control of temperature within the abdomino-pelvic cavity during treatment, particularly during hyperthermic peritoneal perfusion for the treatment of peritoneal dissemination of intra-abdominal cancers and other related clinical situations. Additionally, by permitting repeated access to the abdominal cavity, the apparatus is adapted for non-oncologic use in the management of serious intra-abdominal infections and treatment of intra-abdominal sepsis, peritonitis and pancreatitis.

Although the preferred embodiments of the present invention have been disclosed for illustrative purposes, those skilled in the art will appreciate that various modifications, additions and substitutions are possible without departing from the scope and spirit of the invention as disclosed in the accompanying claims. Additionally, although in the preferred embodiments the shape of the containment vessel and the edges of the cranial and caudal openings are described as elliptical and semi-elliptical, respectively, those skilled in the art will appreciate that these shapes can also be circular, rectangular, or compound shapes.

What is claimed is:

1. An abdomino-pelvic perfusion and lavage apparatus to which a skin surrounding an incision made through an abdominal wall of a patient can be attached and suspended, comprising:

a containment vessel impermeable to water and air, having a wall having a base, wherein said wall has an upper end with a perimeter edge which defines an upper opening, a lower end with a perimeter edge which defines a base opening, a cranial end with a perimeter edge which defines an opening, a caudal end with a perimeter edge which defines an opening;

a plurality of fluid ports capable of providing fluid communication through said wall of said containment vessel;

a scaffolding carried by said containment vessel adapted for supporting and elevating the skin surrounding the incision made through the abdominal wall of the patient, an elevated skin forming a well above, and extending into, an abdomino-pelvic cavity;

said containment vessel being capable of being carried by a table on which the patient is positioned.

2. The abdomino-pelvic perfusion and lavage apparatus of claim 1, wherein said scaffolding comprises:

a support ring for connecting to the skin surrounding the incision made through the abdominal wall of the patient;

at least one connector for connectively disposing between the skin surrounding the incision made through the abdominal wall of the patient and said support ring;

a suspension for carrying said support ring adapted to be disposed superior to the patient's abdominal wall and carried by said wall of said containment vessel;

wherein said support ring defines a shape of an open upper end of the well formed by said elevated skin when said support ring is suspended from said suspension.

3. The abdomino-pelvic perfusion and lavage apparatus of claim 2, wherein said suspension is carried by an inner surface of said wall of said containment vessel.

4. The abdomino-pelvic perfusion and lavage apparatus of claim 2, wherein said suspension is carried by said perimeter edge of said upper end of said wall of said containment vessel.

5. The abdomino-pelvic perfusion and lavage apparatus of claim 2, wherein said support ring forms a closed loop.

6. The abdomino-pelvic perfusion and lavage apparatus of claim 2, wherein said support ring forms an open loop.

7. The abdomino-pelvic perfusion and lavage apparatus of claim 3, wherein said support ring can be connected to the skin surrounding the incision made through the abdominal wall of the patient before said support ring is suspended from said suspension.

8. The abdomino-pelvic perfusion and lavage apparatus of claim 2, wherein said support ring can be connected to the skin surrounding the incision made through the abdominal wall of the patient after said support ring is suspended from said suspension.

9. The abdomino-pelvic perfusion and lavage apparatus of claim 2, wherein:

said support ring can be fully or partially connected to the skin surrounding the incision made through the abdominal wall of the patient before said support ring is suspended from said suspension; and said support ring can be fully or partially connected to the skin surrounding the incision made through the abdominal wall of the patient after said support ring is suspended from said suspension.

10. The abdomino-pelvic perfusion and lavage apparatus of claim 1, wherein said scaffolding comprises:

a support structure disposed around an interior perimeter of said wall of said containment vessel adapted to be superior to the patient's abdominal wall; and at least one connector for connectively disposing between the skin surrounding the incision made through the abdominal wall of the patient and said support structure.

11. The abdomino-pelvic perfusion and lavage apparatus of claim 10, wherein said support structure is adapted to frame the incision made through the abdominal wall of the patient.

12. The abdomino-pelvic perfusion and lavage apparatus of claim 10, wherein said support structure is comprised of rods inserted through a plurality of sealable openings communicating through said wall of said containment vessel.

13. The abdomino-pelvic perfusion and lavage apparatus of claim 12, further comprising a plurality of opening-seals for forming air and watertight seals in said plurality of sealable openings thereby forming a barrier to aerosols so that chemotherapy can be used without exposing personnel to chemotherapy aerosols, and so that the containment vessel can be left in place on the patient who can then be returned to a surgical intensive care unit for follow-up examinations and repeated lavage procedures without necessitating use of an operating room except for closure of the incision made through the abdominal wall of the patient.

14. The abdomino-pelvic perfusion and lavage apparatus of claim 10, wherein said support structure is comprised of rods carried by an inner surface of said wall of said containment vessel.

15. The abdomino-pelvic perfusion and lavage apparatus of claim 10, wherein said support structure is integral with an inner surface of said wall of said containment vessel.

16. The abdomino-pelvic perfusion and lavage apparatus of claim 1, further comprising at least one seal for forming an air and watertight seal between said containment vessel and a torso of the patient, thereby forming a barrier to aerosols so that chemotherapy can be used without exposing personnel to chemotherapy aerosols, and so that said containment vessel can be left in place on the patient who can then be returned to an intensive care unit for follow-up examinations and repeated lavage procedures without introducing bacterial pathogens and without necessitating use of an operating room except to close the incision made through the abdominal wall of the patient.

17. The abdomino-pelvic perfusion and lavage apparatus of claim 16, wherein said at least one seal further comprises:
   a first seal disposed proximate to said perimeter edge of said cranial end; and
   a second seal disposed proximate to said perimeter edge of said caudal end.

18. The abdomino-pelvic perfusion and lavage apparatus of claim 1, further comprising:
   a base seal disposed proximate to said base of said containment vessel, said base seal for forming an air and watertight seal between said containment vessel and the table, thereby forming a barrier to aerosols so that chemotherapy can be used without exposing personnel to chemotherapy aerosols, and so that said containment vessel can be left in place on the patient who can then be returned to a surgical intensive care unit for follow-up examinations and repeated lavage procedures without introducing bacterial pathogens and without necessitating use of an operating room except to close the incision made through the abdominal wall of the patient.

19. The abdomino-pelvic perfusion and lavage apparatus of claim 1, wherein pneumatic communication can be established through at least one of said plurality of fluid ports.

20. The abdomino-pelvic perfusion and lavage apparatus of claim 19, further comprising an air evacuation means, in pneumatic communication with said at least one of said plurality of fluid ports, for removing chemotherapy aerosols from within said containment vessel.

21. The abdomino-pelvic perfusion and lavage apparatus of claim 20, wherein said air evacuation means is a smoke evacuator system.

22. The abdomino-pelvic perfusion and lavage apparatus of claim 1 wherein said plurality of fluid ports are sealable.

23. The abdomino-pelvic perfusion and lavage apparatus of claim 22 further comprising a plurality of port-seals for selectively sealing said plurality of fluid ports thereby forming a barrier to aerosols so that chemotherapy can be used without exposing personnel to chemotherapy aerosols, and said containment vessel can be left in place on the patient who can then be returned to an intensive care unit for follow-up examinations and repeated lavage procedures without introducing bacterial pathogens and without necessitating use of an operating room except to close the incision made through the abdominal wall of the patient.

24. An abdomino-pelvic perfusion and lavage apparatus to which a skin surrounding an incision made through an abdominal wall of a patient can be attached and suspended, comprising:
   a containment vessel impermeable to water and air, having a wall having a base, wherein said wall has an upper end with a perimeter edge which defines an upper opening, a lower end with a perimeter edge which defines a base opening, a cranial end with a perimeter edge which defines an opening, a caudal end with a perimeter edge which defines an opening;
   a plurality of fluid ports capable of providing fluid communication through said wall of said containment vessel;
   a scaffolding carried by said containment vessel adapted for supporting and elevating the skin surrounding the incision made through the abdominal wall of the patient, an elevated skin forming a well above, and extending into, an abdomino-pelvic cavity;
   wherein hydraulic communication can be established through at least one of said plurality of fluid ports.

25. The abdomino-pelvic perfusion and lavage apparatus of claim 24, wherein:
   at least one of said plurality of fluid ports further comprises at least one inflow port; and
   at least one of said plurality of fluid ports further comprises at least one outflow port.

26. The abdomino-pelvic perfusion and lavage apparatus of claim 25, further comprising:
   a fluid supply reservoir;
   a f first pump in hydraulic communication with the fluid supply reservoir and said at least one inflow port to provide a perfusion fluid from said supply reservoir to said containment vessel;
   a second pump in hydraulic communication with the fluid supply reservoir and said at least one outflow port to provide the perfusion fluid from said containment vessel back to the supply reservoir; and
   a heater in thermal communication with a fluid containing means to heat the perfusion fluid to a temperature of about 30° C. to about 50° C. during use of said containment vessel in hyperthermic peritoneal perfusion.

27. The abdomino-pelvic perfusion and lavage apparatus of claim 26, further comprising:
   at least one inflow tube connected to said at least one inflow port for providing the perfusion fluid to the well in the abdomino-pelvic cavity; and
   at least one drain tube connected to said at least one outflow port having a distal intake end for extending into the abdomino-pelvic cavity of the patient for providing the perfusion fluid from the well.

28. The abdomino-pelvic perfusion and lavage apparatus of claim 27, further comprising:
   at least one temperature sensor positioned in proximity with the distal intake end of the at least one drain tube, said at least one temperature sensor being in communication with a thermostatic control; and
   said thermostatic control being in communication with said heater.

29. An abdomino-pelvic perfusion and lavage apparatus to which a skin surrounding an incision made through an abdominal wall of a patient can be attached and suspended, comprising:
   a containment vessel impermeable to water and air, having a wall having a base, wherein said wall has an upper end with a perimeter edge which defines an upper opening, a lower end with a perimeter edge which defines a base opening, a cranial end with a perimeter edge which defines an opening, a caudal end with a perimeter edge which defines an opening;
   a plurality of fluid ports capable of providing fluid communication through said wall of said containment vessel;
   a scaffolding carried by said containment vessel adapted for supporting and elevating the skin surrounding the incision made through the abdominal wall of the patient, an elevated skin forming a well above, and extending into, an abdomino-pelvic cavity;

at least one removable cover capable of being secured and sealed over said upper opening of said containment vessel to enclose the well therein, thereby forming a barrier to aerosols so that chemotherapy can be used without exposing personnel to chemotherapy aerosols, and so that said containment vessel can be left in place on the patient who can then be returned to an intensive care unit for follow-up examinations and repeated lavage procedures without introducing bacterial pathogens and without necessitating use of an operating room except for closure of the incision made through the abdominal wall of the patient.

30. An abdomino-pelvic perfusion and lavage apparatus to which a skin surrounding an incision made through an abdominal wall of a patient can be attached and suspended, comprising:

a containment vessel impermeable to water and air, having a wall having a base, wherein said wall has an upper end with a perimeter edge which defines an upper opening, a lower end with a perimeter edge which defines a base opening, a cranial end with a perimeter edge which defines an opening, a caudal end with a perimeter edge which defines an opening;

a plurality of fluid ports capable of providing fluid communication through said wall of said containment vessel, said containment vessel being capable of being carried by a table on which the patient is positioned;

a scaffolding carried by said containment vessel adapted for supporting and elevating the skin surrounding the incision made through the abdominal wall of the patient whereby said elevated skin forms a well above, and extending into, an abdomino-pelvic cavity;

at least one removable cover capable of being secured and sealed over said upper opening of said containment vessel to enclose the well therein, thereby forming a barrier to aerosols so that chemotherapy can be used without exposing personnel to chemotherapy aerosols, and said containment vessel can be left in place on the patient who can then be returned to an intensive care unit for follow-up examinations and repeated lavage procedures without introducing bacterial pathogens and without necessitating use of an operating room except to close the incision made through the abdominal wall of the patient;

a plurality of port-seals for sealing said plurality of fluid ports;

a first seal disposed proximate to said perimeter edge of said cranial end to seal fluid communication between said containment vessel and a torso of the patient;

a second seal disposed proximate to said perimeter edge of said caudal end to seal fluid communication between said containment vessel and a torso of the patient; and a base seal disposed proximate to said base of said containment vessel to seal fluid communication between said containment vessel and the table.

31. A method for perfusing, lavaging and irrigating an abdomino-pelvic cavity, comprising:

placing a containment vessel impermeable to water and air over a patient, said containment vessel having a wall having a base, said wall having an upper end with a perimeter edge which defines an upper opening, a lower end with a perimeter edge which defines a base opening, a cranial end with a perimeter edge which defines an opening, a caudal end with a perimeter edge which defines an opening, and a plurality of fluid ports capable of providing fluid communication through said wall, and a scaffolding carried by said containment vessel adapted for supporting and elevating a skin surrounding an incision made through an abdominal wall of the patient;

upwardly extending skin edges surrounding the incision made through the abdominal wall of the patient and connecting the skin edges to said scaffolding to form a well above and extending into the abdomino-pelvic cavity of the patient;

introducing a perfusion fluid through said wall of said containment vessel into the well for treatment of intra-abdominal tissues;

draining the perfusion fluid from the abdomino-pelvic cavity to flush fibrinous debris and other intra-abdominal contaminants from the abdomino-pelvic cavity.

32. The method of claim 31, including the steps of:
inserting a surgeon's hands through said upper opening in said containment vessel into the abdomino-pelvic cavity;
manipulating the perfusion fluid and the intra-abdominal tissues;
debriding narrow margins of excisions;
removing fibrinous accumulations; and
visually inspecting all bowel surfaces.

33. The method of claim 31, including the step of adding drugs to a lavage fluid for treatment of diseases, infection, conditions, and other disorders in the abdomino-pelvic cavity.

34. The method of claim 33, including the step of sealing a cover over said containment vessel and performing a lavage for up to 5–10 days.

35. The method of claim 34, including the steps of:
selectively opening said cover; and
inserting a surgeon's hands through said upper opening in said containment vessel into the abdomino-pelvic cavity;
manipulating the perfusion fluid and the intra-abdominal tissues;
debriding narrow margins of excisions;
removing fibrinous accumulations; and
visually inspecting all bowel surfaces.

36. The method as claimed in claim 35, including the step of evacuating aerosols and gasses from an interior space within said containment vessel.

37. The method as claimed in claim 36, including the step of activating a means for evacuating the aerosols and gasses when said cover is opened.

38. The method of claim 33, including the step of heating the perfusion fluid to a desired temperature before it is introduced into the abdomino-pelvic cavity to increase a toxicity of the drugs to a disease being treated.

39. The method of claim 38, including the step of sealing a cover over said containment vessel and performing a lavage for up to 5–10 days.

40. The method of claim 39, including the steps of:
selectively opening said cover;
inserting a surgeon's hands through said upper opening in said containment vessel into the abdomino-pelvic cavity;
manipulating the perfusion fluid and the intra-abdominal tissues;
debriding narrow margins of excisions;
removing fibrinous accumulations; and
visually inspecting all bowel surfaces.

41. The method as claimed in claim 40, including the step of evacuating aerosols and gasses from an interior space within said containment vessel.

42. The method as claimed in claim 41, including the step of activating a means for evacuating the aerosols and gasses when said cover is opened.

43. The method as claimed in claim 35 further comprising the step of performing or continuing a surgical procedure in the patient's abdominal cavity through said upper opening.

44. The method as claimed in claim 43 wherein the surgical procedure is conducted while chemotherapy or drugs are being administered in the well.

45. A method for perfusing an abdomino-pelvic cavity, comprising:

placing a containment vessel impermeable to water and air over a patient, said containment vessel having a wall having a base, said wall having an upper end with a perimeter edge which defines an upper opening, a lower end with a perimeter edge which defines a base opening, a cranial end with a perimeter edge which defines an opening, a caudal end with a perimeter edge which defines an opening, and a plurality of fluid ports capable of providing fluid communication through said wall, and a scaffolding carried by said containment vessel adapted for supporting and elevating a skin surrounding an incision made through an abdominal wall of the patient;

upwardly extending skin edges surrounding the incision made through the abdominal wall of the patient and connecting the skin edges to said scaffolding to form a well above and extending into the abdomino-pelvic cavity of the patient;

introducing a perfusate through said wall of said containment vessel into the well for perfusing intra-abdominal tissues;

draining the perfusate from the abdomino-pelvic cavity to remove fibrinous debris and other intra-abdominal contaminants from the abdomino-pelvic cavity.

\* \* \* \* \*

UNITED STATES PATENT AND TRADEMARK OFFICE
CERTIFICATE OF CORRECTION

PATENT NO. : 6,383,162 B1
DATED : May 7, 2002
INVENTOR(S) : Paul H. Sugarbaker

It is certified that error appears in the above-identified patent and that said Letters Patent is hereby corrected as shown below:

<u>Column 7,</u>
Line 2, change "3" to -- 2 --

<u>Column 26,</u>
Line 4, change "a f first" to -- a first --

Signed and Sealed this

Eighteenth Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,383,162 B1
DATED : May 7, 2002
INVENTOR(S) : Paul H. Sugarbaker

It is certified that error appears in the above-identified patent and that said Letters Patent is hereby corrected as shown below:

Column 14,
Line 10, change "3" to -- 2 --

Column 16,
Line 17, change "a f first" to -- a first --

Signed and Sealed this

Fourth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,383,162 B1  
DATED        : May 7, 2002  
INVENTOR(S)  : Paul H. Sugarbaker It is certified that error appears in the above-identified patent and that said Letters Patent is hereby corrected as shown below:

Column 14,  
Line 10, change "3" to -- 2 --

Column 16,  
Line 17, change "a f first" to -- a first --

This certificate supersedes Certificate of Correction issued June 18, 2002 and February 4, 2003.

Signed and Sealed this

First Day of July, 2003

JAMES E. ROGAN  
*Director of the United States Patent and Trademark Office*